United States Patent [19]

Sibalis

[11] Patent Number: 5,653,682

[45] Date of Patent: *Aug. 5, 1997

[54] DISPOSABLE AND/OR REPLENISHABLE TRANSDERMAL DRUG APPLICATORS AND METHOD OF MANUFACTURING SAME

[75] Inventor: Dan Sibalis, Stony Brook, N.Y.

[73] Assignee: Drug Delivery Systems, Inc., New York, N.Y.

[*] Notice: The term of this patent shall not extend beyond the expiration date of Pat. No. 4,883,457.

[21] Appl. No.: 327,624

[22] Filed: Oct. 24, 1994

Related U.S. Application Data

[62] Division of Ser. No. 949,721, Sep. 23, 1992, Pat. No. 5,358,483, which is a division of Ser. No. 380,196, Jul. 14, 1989, Pat. No. 5,167,617, which is a continuation-in-part of Ser. No. 58,527, Jun. 5, 1987, Pat. No. 4,883,457, and a division of Ser. No. 105,889, Oct. 7, 1987, Pat. No. 4,856,188, which is a division of Ser. No. 807,234, Dec. 10, 1985, Pat. No. 4,731,926, and a continuation-in-part of Ser. No. 702,486, Feb. 19, 1985, abandoned, and a continuation-in-part of Ser. No. 660,192, Oct. 12, 1984, Pat. No. 4,622,031, and Ser. No. 524,252, Aug. 18, 1983, Pat. No. 4,557,723.

[51] Int. Cl.$^6$ ............................................ A61N 1/30

[52] U.S. Cl. ................................. 604/20; 607/149

[58] Field of Search ......................... 604/20–21, 890.1, 604/290; 607/129, 149–152; D24/189

[56] References Cited

U.S. PATENT DOCUMENTS

| | | | |
|---|---|---|---|
| 4,557,723 | 12/1985 | Sibalis | 604/20 |
| 4,622,031 | 11/1986 | Sibalis | 604/20 |
| 4,883,457 | 11/1989 | Sibalis | 604/20 |
| 5,358,483 | 10/1994 | Sibalis | 604/20 |

*Primary Examiner*—Mark Bockelman
*Attorney, Agent, or Firm*—Kathleen L. Maher

[57] ABSTRACT

An electrically/battery powered transdermal drug applicator comprising a flexible non-conductive substrate with a plurality of conductive coated areas, the conductive coated areas forming drug reservoir electrodes, and a plurality of drug reservoirs separated by occlusive adhesive dams and in electrical contact with said drug reservoir electrodes. The battery is connected to the electrodes of the drug reservoirs and said applicator including electrical current conditioning means, with a conformal cover adhesively secured to said transdermal drug applicator and with a release liner covering and protecting said plurality of drug reservoirs until use.

17 Claims, 6 Drawing Sheets

DISPOSABLE AND/OR REPLENISHABLE TRANSDERMAL DRUG APPLICATORS AND METHOD OF MANUFACTURING SAME

RELATED U.S. PATENT APPLICATIONS

This application is a division of Ser. No. 07/949,721 filed Sep. 23, 1992 now U.S. Pat. No. 5,358,483, which is a division of Ser. No. 07/380,196 filed Jul. 14, 1989, now U.S. Pat. No. 5,167,617, which is a cip of Ser. No. 07/058,527 filed Jun. 5, 1987 now U.S. Pat. No. 4,883,457 and a division of Ser. No. 105,889, filed Oct. 7, 1987 now U.S. Pat. No. 4,856,188, which is a division of Ser. No. 06/807,234 filed Dec. 10, 1985 now U.S. Pat. No. 4,731,926, which is a cip of PCT/US85/01075 filed Jun. 10, 1985, and a cip of Ser. No. 06/702,486 filed Feb. 19, 1985 now abandoned, which is a cip of PCT/US85/00080 filed Jan. 17, 1985, and a cip of Ser. No. 06/660,192 filed Oct. 12, 1984 now U.S. Pat. No. 4,622,031 and a cip of Ser. No. 06/524,252 filed Aug. 18, 1983 now U.S. Pat. No. 4,557,723.

INCORPORATION BY REFERENCE

This application incorporates by reference my earlier filings, Ser. No. PCT/US85/01075, filed Jun. 10, 1985; and Ser. No. 06/702,486, filed Feb. 19, 1985 now U.S. Pat. No. 4,662,031, complete copies of which are attached hereto and expressly made a part of this disclosure as pages A1 through A-76 as a matter of convenience.

FIELD OF THE INVENTION

This invention relates to disposable as well as replenishable transdermal drug applicators which are electrically powered, and to methods for making such constructions. A complete electrical circuit is made through the skin once the drug applicator is adhered thereto, whereby at least one physico/chemical mass transfer phenomenon takes place causing the drug or medicament to migrate through the skin.

BACKGROUND OF THE INVENTION

Reference to or disclosure of devices for transdermal delivery of drugs by application of electrical current through the skin of a person or animal are shown in the following United States patents:

| | |
|---|---|
| 385,556 | 4,243,052 |
| 486,902 | 4,325,367 |
| 588,479 | 4,367,745 |
| 2,493,155 | 4,419,091 |
| 2,267,162 | 4,474,570 |
| 2,784,715 | 4,406,658 |
| 3,163,166 | 4,314,554 |
| 3,289,671 | 4,166,457 |
| 3,547,107 | 4,239,052 |
| 3,677,268 | 4,290,878 |
| 4,008,721 | 4,164,226 |
| 4,141,359 | 4,362,645 |
| 4,239,046 | 4,273,135 |

The following foreign patents refer to or disclose transdermal delivery devices:
EPA 0060452
DE 290202183
DE 3225748
EPA 0058920
UK 2104388

DESCRIPTION OF THE PREFERRED EMBODIMENTS

It should also be noted that as a convenience in the following description of the invention, like numerals are representative of similar elements common to the various embodiments of the invention.

Figure 1:
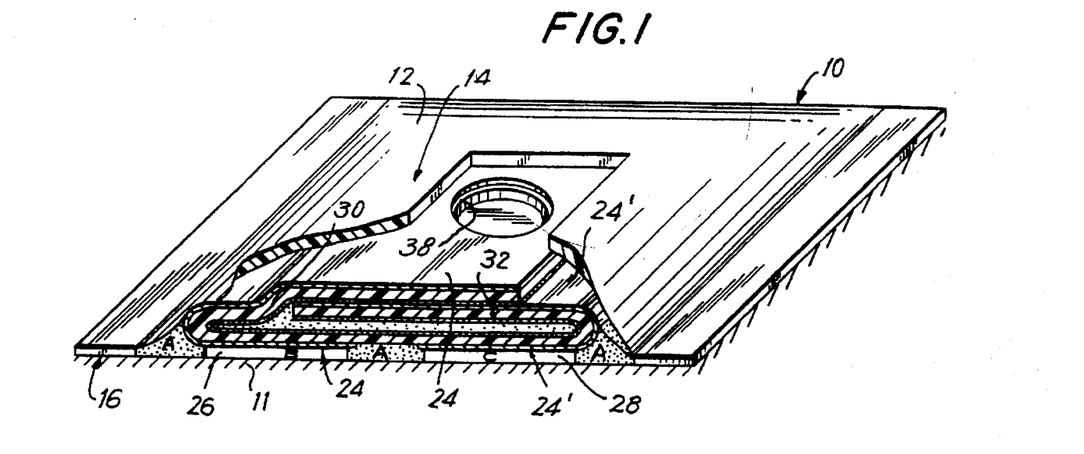
FIG. 1 is a perspective view, partially cut away, so as to illustrate the innards of a self-contained drug applicator of the invention.
Figure 2:
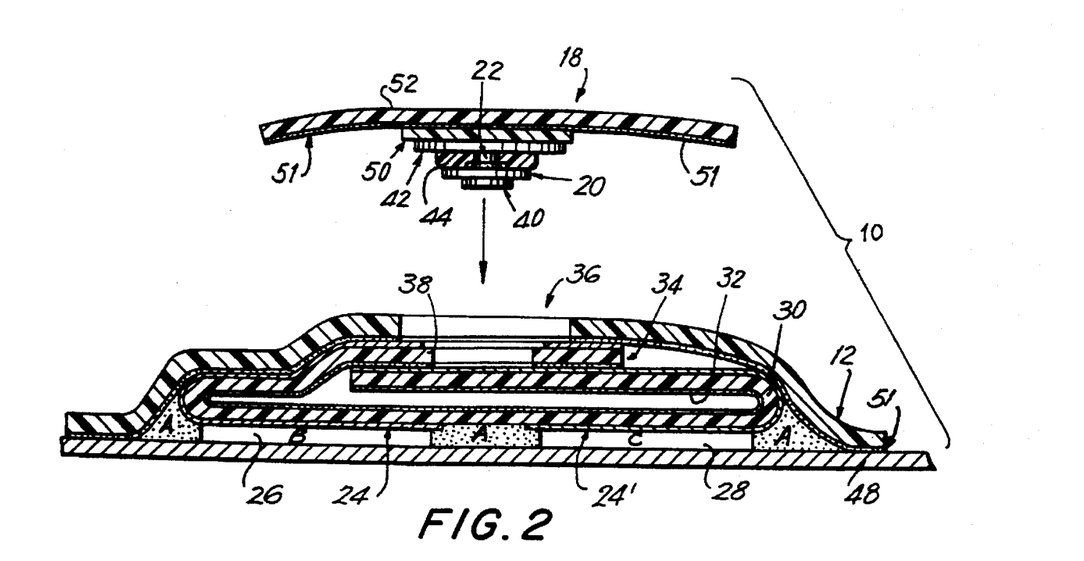
FIG. 2 is a longitudinal cross-sectional view of the drug applicator of FIG. 1, and also illustrating in exploded view a reusable power supply which may be provided with a programmable control and wrist watch mounting.

Referring now to FIGS. 1–2, there is shown a transdermal drug applicator 10 which is adhered to the skin 11 comprising an outer cover 12 with a centrally raised portion 14 and a peripheral sealed area or lip portion 16. Such an applicator is of the replaceable type having provision for connection to a reusable power supply 18 which may be, if desired, part of a wrist watch mounting having optionally a programmable control device such as more particularly described and claimed in said aforementioned earlier filed patent application, Ser. No. PCT/US85/01075, filed Jun. 10, 1985.

Power supply 18 comprises a suitable disc battery 20 having electrodes or terminals on opposite sides thereof.

One battery electrode is electrically connected to current conditioning or electronic conditioning means 22 and by means of suitable snap-on or other type of mechanical connectors (silver-plated Velcro connections manufactured by Velcro Corporation of America) or by conductive and reusable adhesives; and the battery electrodes are in turn connected to conductors 24, 24' extending from drug reservoirs 26, 28. The conductors 24, 24' are suitably conductive surfaces or coatings on a flexible plastic substrate 30 which is non-conductive, permeable, stable and otherwise compatible with drugs, adhesives, the skin and any other materials from which the device is fabricated. When bent and folded back upon itself; the plastic substrate 30 and conductive surfaces bring the electrical contacts to the top side of the drug applicator where the electrical connections are to be made with the reusable power supply 18. The adhesive coating 32 on the inside (and topside) of the plastic substrate 30 secures together the mating surfaces as well as the overlapping edge or end 34 which is provided with a suitable slot or aperture 36 representing a nest or well area for receiving the power supply 18 and its electrical connectors. A small peripheral clearing 38 about the aperture 36 represents an insulating guard area to preclude any possibility of shorting out. Thus, the lower electrode 40 and upper electrode 42 of the battery directly or indirectly make electrical contact with conductors 24, 24'. Suitable insulating material 44 surrounds the current or electronic conditioning means 22, as well as forms the dam separating the drug reservoirs 26, 28 and provides the end seals for not only the side of longitudinal edges but also for the transverse edges of the transdermal drug applicator. A conformable cover 12 protects the entire device and may be suitably of a skin tone or color and the like appearance.

Should snaps or other type of material fasteners be employed, it is preferable if the disposition of same is such that the snaps are not symmetrically laid out as such arrangement would ensure that the power supply could only be mated in a single manner.

With the drug applicator shown being of electrode/reservoir construction of the side by side type, the cover need not be conductive as the lip portion merely serves as a peripheral seal and not a return electrode. However, it will be appreciated that the invention is also applicable to drug applicators of the "matted" frame construction where the lip portion serves as the return or inactive electrode. In such case, then the conformable cover must also be conductive. Electro-kinetic mass transfer processes require an electric power source, and in the case of electrophoresis an ionized drug migrates from the drug applicator patch through the skin and into the blood stream, whereas in the case of electroosmosis, a fluid carrier, such as water is likewise transported across the skin and into the blood stream carrying along with it any and all dissolved constituents (ionized drugs or otherwise). Either or both of these two physicochemical phenomena may jointly work together or independently in transdermally carrying a drug or drugs across the skin in a desired dosage release and/or relatively steady pattern.

The application of an electric field across the skin greatly enhances the skin permeability to various drugs.

Prior to the attachment to the skin, a suitable release liner 48 is removed leaving the two drug reservoirs, insulating dam and peripheral seals free to adhere to the skin.

It should also be understood that the power supply 18 is supported by a like plastic substrate 50 which is in turn suitably adhesively secured by adhesive 51 to a small conformal cover 52 which neatly covers over and seals off the apertured area where the electrical connections are made. This ensures that the device can be worn at all times; such as in the rain or in the shower or bath.

Figure 2A:
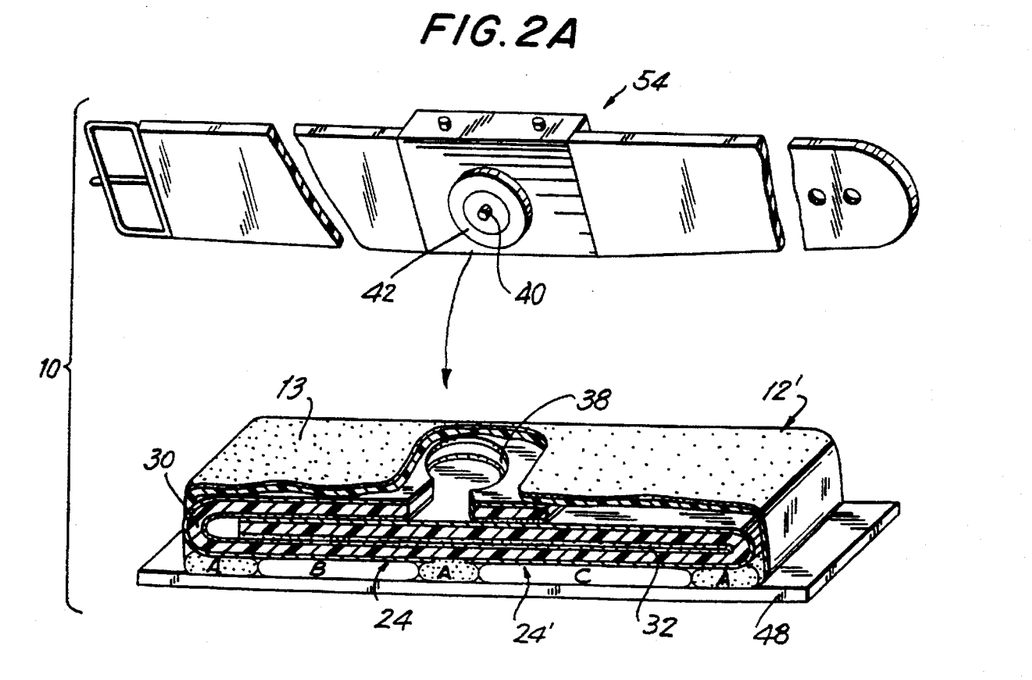
FIG. 2A is a view similar to FIG. 2, but shown perspectively, in which the power supply and the programmable control are contained within a wrist watch mounting having concentric connectors.

If desired, the reusable power supply 18 may be part of a wrist watch 54, as shown in FIG. 2A, having a programmable computer with concentric conductive adhesive connectors 40, 42, such as previously disclosed in said earlier patent filing with like electrical connections and mechanical securement being provided where needed to achieve such packaged construction. The main difference between the disposable drug applicators shown in FIGS. 2 and 2A is that the conformal cover means 12' of FIG. 2A is coated with an adhesive layer 13. Such adhesive layer 13 allows removal of the drug applicator and replacement same as adhesive 51 in FIG. 2.

Figure 3:
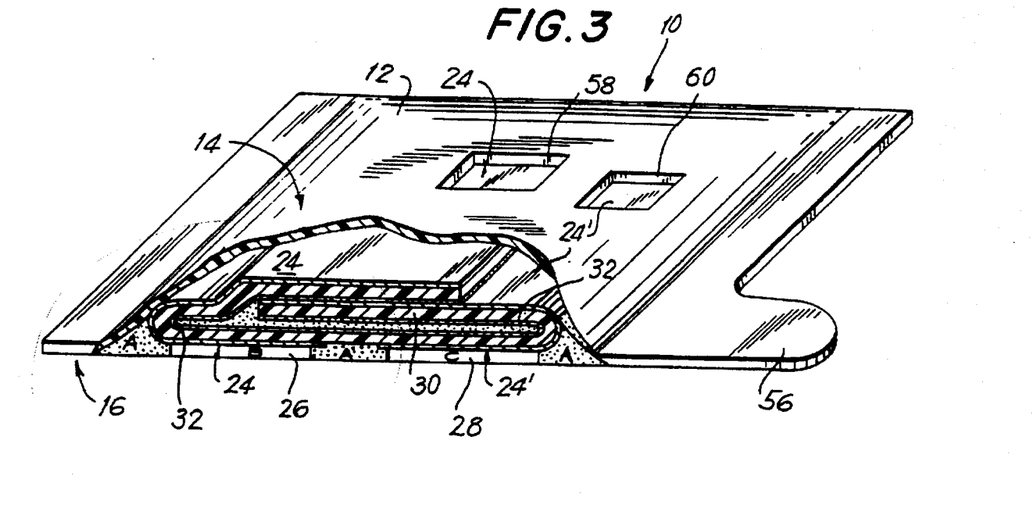
FIG. 3 is another perspective view similar to FIG. 1, but showing an alternate construction having a pair of off-center apertures or slots for the electrical connections in lieu of concentric electrical contacts made through the use of a single center aperture so as to enable the mounting of a new drug applicator to the reusable power supply in a keyed or polarized manner.

The alternate construction shown in FIG. 3 simply adds the feature of an optimal tab 56 for the release liner or paper, and the use of offset apertures 58 and 60 for mating with the conductive adhesive contacts at the bottom of battery 20 and the extended substrate 50 which may be offset in a manner to provide just side to side connection in lieu of concentric or symetric connections.

Figure 4:
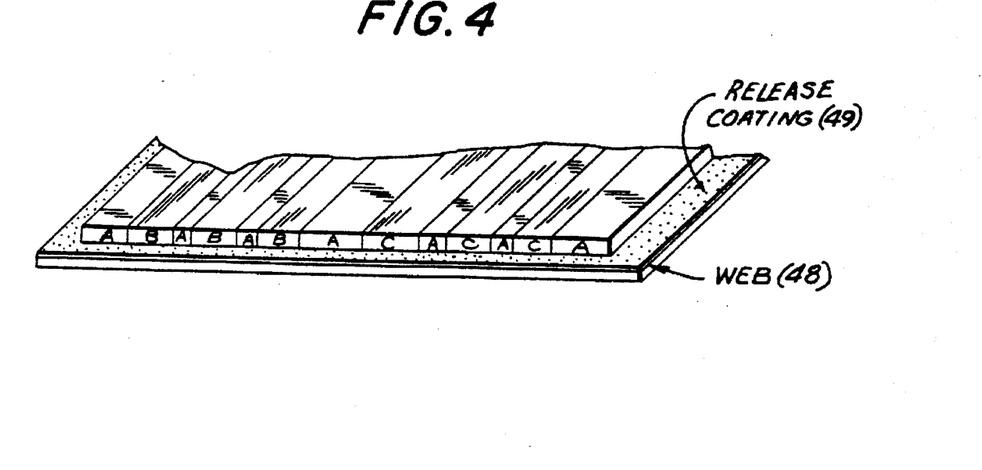
FIGS. 4 and 5 are fragmentary perspective views of typical configurations of drug electrodes/reservoirs provided on endless web substrates fed from rolled stock material, with occlusive adhesive dams separating the drug reservoirs longitudinally, as well as transversely.
Figure 5:
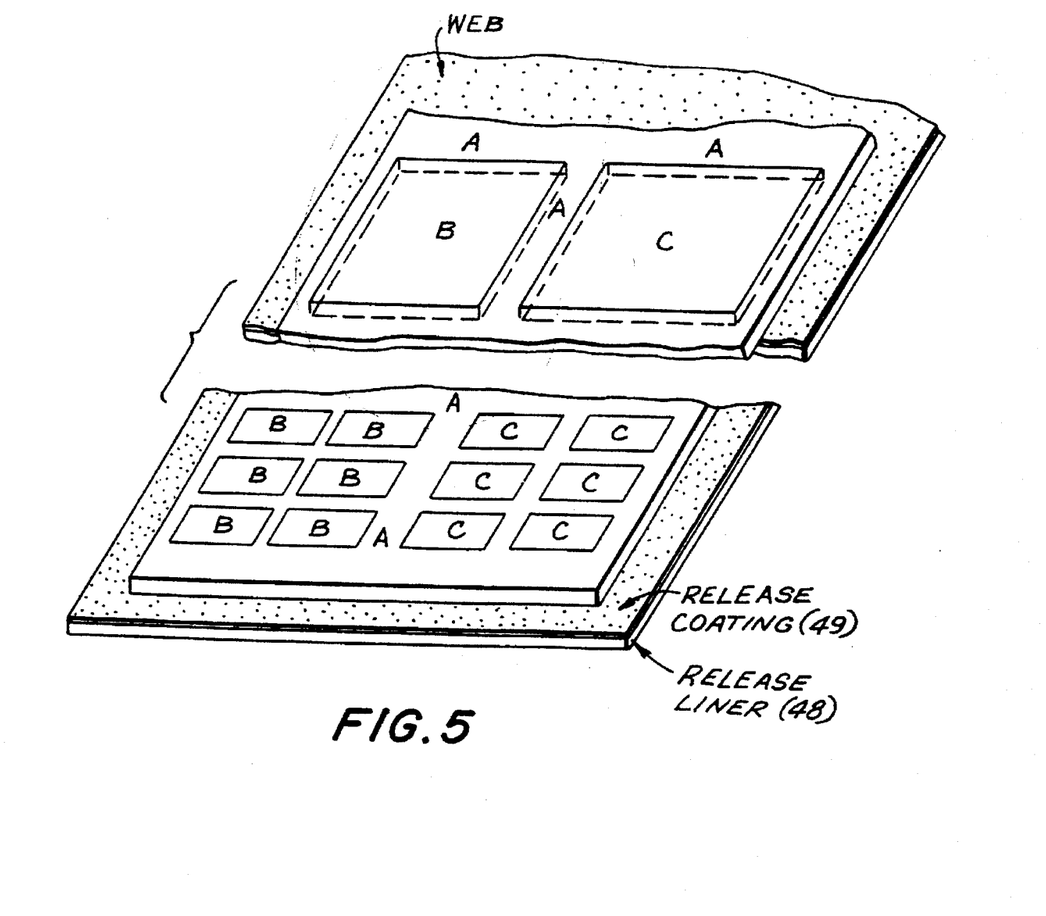
Figure 6A:
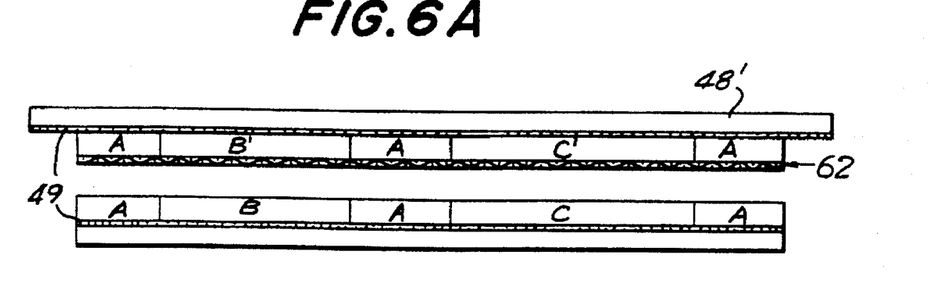
FIGS. 6A, 6B and 7A, 7B respectively illustrate diagrammatically typical assemblies of drug electrodes/reservoirs forming larger reservoir means; or forming drug gradient with layers of both high and low drug concentration within reservoirs separated by a semipermeable membrane or reinforcing scrim.
Figure 6B:
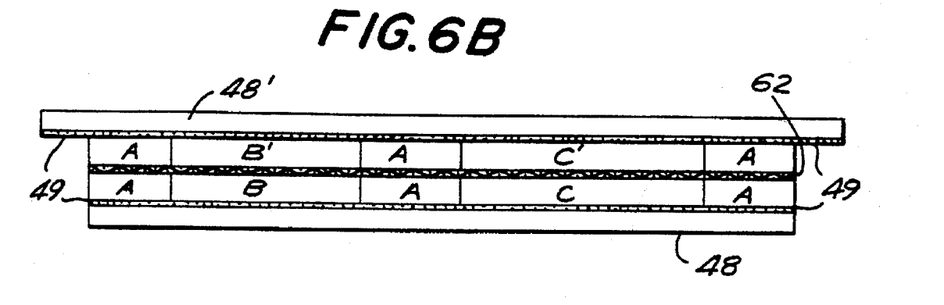
Figure 7A:
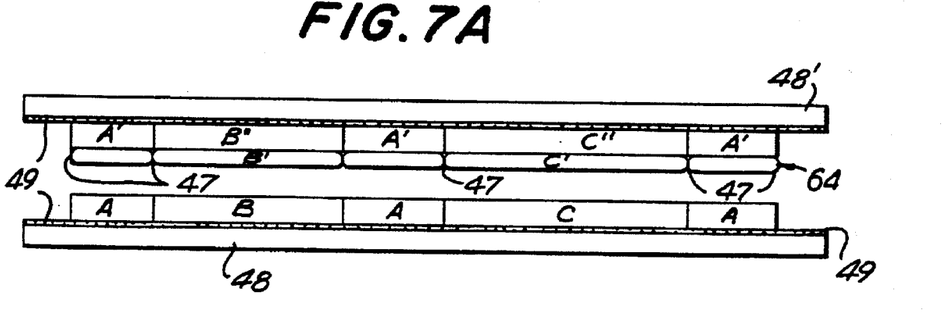
Figure 7B:
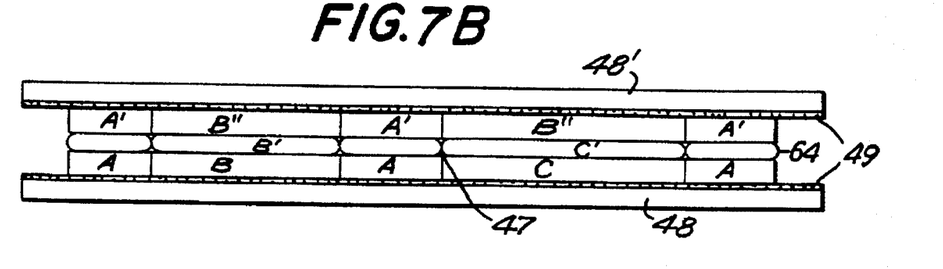
Figure 8:
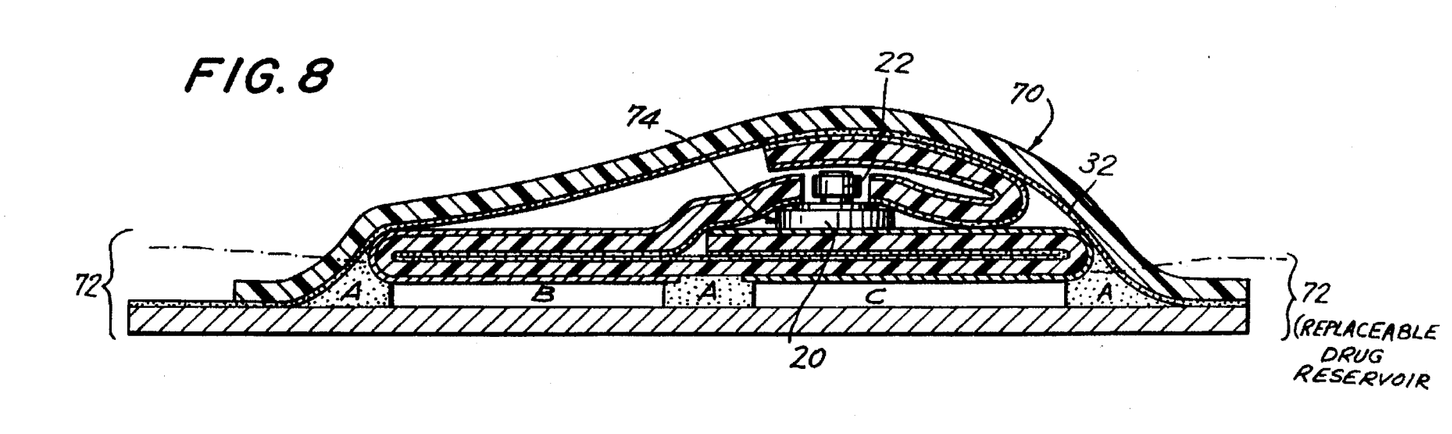
FIG. 8 is a cross-sectional view of a disposable drug applicator with a separate subassemblied power source and electrical conditioning means adhesively assembled along their electrodes to any one typical drug electrode/reservoir assemblies shown in FIGS. 6–7.
Figure 9:
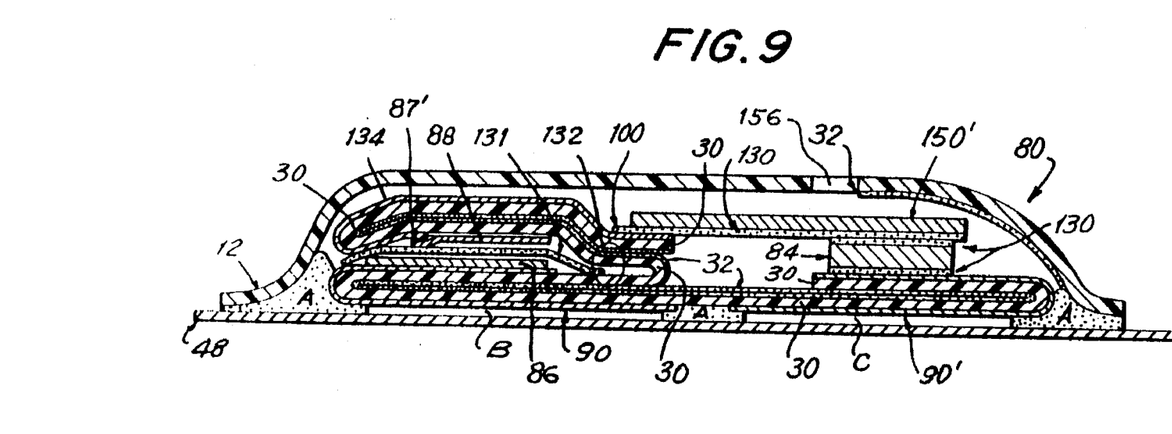
FIG. 9 is a cross-sectional view of an alternate construction having similarly optionally replaceable drug reservoirs (electrodes/reservoirs), and with flat batteries forming a sub-assembly with electrical connections to electronic conditioning means.

In FIGS. 4–7, drug sub-assemblies are illustrated for use with the disposable transdermal drug applicators shown in FIGS. 8–9. As shown in FIGS. 4 and 5, the drug reservoirs may be suitable gel layers which can be rolled or otherwise applied to a webbed substrate fed from endless rolled sheet material while being separated between reservoirs and about their extreme edges by applied occlusive adhesive dams. The dams are identified by the Letters A and the drug reservoirs are marked with the letters B representing negative and C representing positive. The "quilt" type pattern where multiple drug reservoirs are employed can be fabricated by repetitive operative steps using a silk screen printing or transfer process. It should also be recognized that the substrate is coated with a suitable release agent 49, such as silicone and when the sub-assembly is combined into a complete transdermal drug applicator or patch, the substrate in effect becomes the release liner.

FIGS. 6A, 6B–7A, 7B illustrate the assembly of two drug applicator sub-assemblies. For example, in FIGS. 6A, 6B, an optional reinforcing web or veil-like material (scrim) 62 may be used to reinforce the gel "drug" reservoirs.

One embodiment uses an open cell foam which is impregnated in different areas with gel drug reservoirs surrounded by occlusive adhesive gel impregnating the same open cell foam. Such a structure allows the construction of a thick replaceable drug reservoir in which the gel will maintain its integrity during manufacturing, the application to and removal from human skin, as well as to the replacement of exhausted drug reservoirs. In manufacture, the open cell foam web may be suitably attached to a release liner, then provided with occlusive adhesive dams which completely penetrate the full thickness of the open cell foam, thus forming or designating the drug reservoir areas which can be subsequently filled in with their respective drug/gel mixtures.

Figure 10:
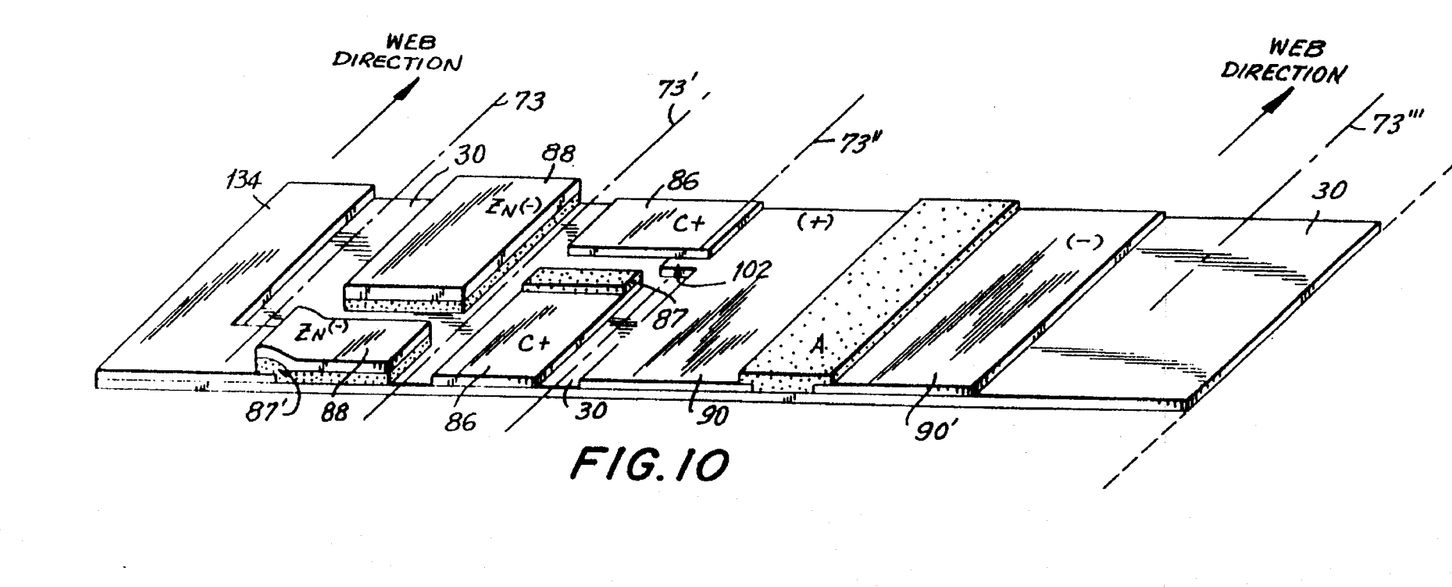
FIG. 10 illustrates an endless such substrate fed from rolled stock material upon which is provided thin sheet electrodes for the flat batteries and other rolled, layered materials for forming the power-source sub-assembly shown in FIG. 9.

As one 48' of the two disposed release liners can be further discarded in production, it can be considered optional, bearing in mind that the gel reservoirs and dams are viscous and retain their shape, and may even be further supported by a reinforcing web 62. FIGS. 7A, 7B simply differ in that a semi-permeable membrane 64 is provided between the two sub-assemblies so that upon assembly, drug reservoirs are formed with areas or zones of different drug concentration or composition. Such a type of drug reservoir is noted to have significant advantages during operation of the transdermal device. Note that appropriate seals can be provided along the semi-permeable membranes at the edges where each reservoir ends by means of heat or by other means to collapse the voids and seal the semipermeable membrane in those areas 47 where the seals are necessary. Alternately, silicone dams could also be used as seals between zones of semi-permeable materials. In addition, the semi-permeable materials may be preimpregnated with drugs or other chemicals which might be employed. These sub-assemblies of FIGS. 4–7 will now be shown and described as assembled onto the sub-assembly of FIG. 10. For purposes of disposability of the drug reservoirs, these sub-assemblies (FIGS. 4–7) are disposable and like replacements may be used to replenish the drug supply.

The disposable drug applicator 70 shown in FIG. 8 comprises an optionally replaceable drug reservoir sub-assembly 72 (any one of FIGS. 4–7) and a further sub-assembly 74 for the power means and electrical conditioning means which assemblies are secured together by suitable conductive adhesives. Sub-assembly 74 comprised essentially of battery 20 and current conditioning means 22 and associated conductive adhesives 40, 42, as best shown in FIG. 2. The electrical circuit running between the drug reservoirs and through the skin is a loop similar to that of FIG. 2, the only difference being the permanent nature of the battery and current/electrical conditioning means in the applicator structure rather than the reusable nature of the FIG. 2 embodiment. However, here just the drug reservoir sub-assembly 72 may be replaced where required.

Figure 8A:
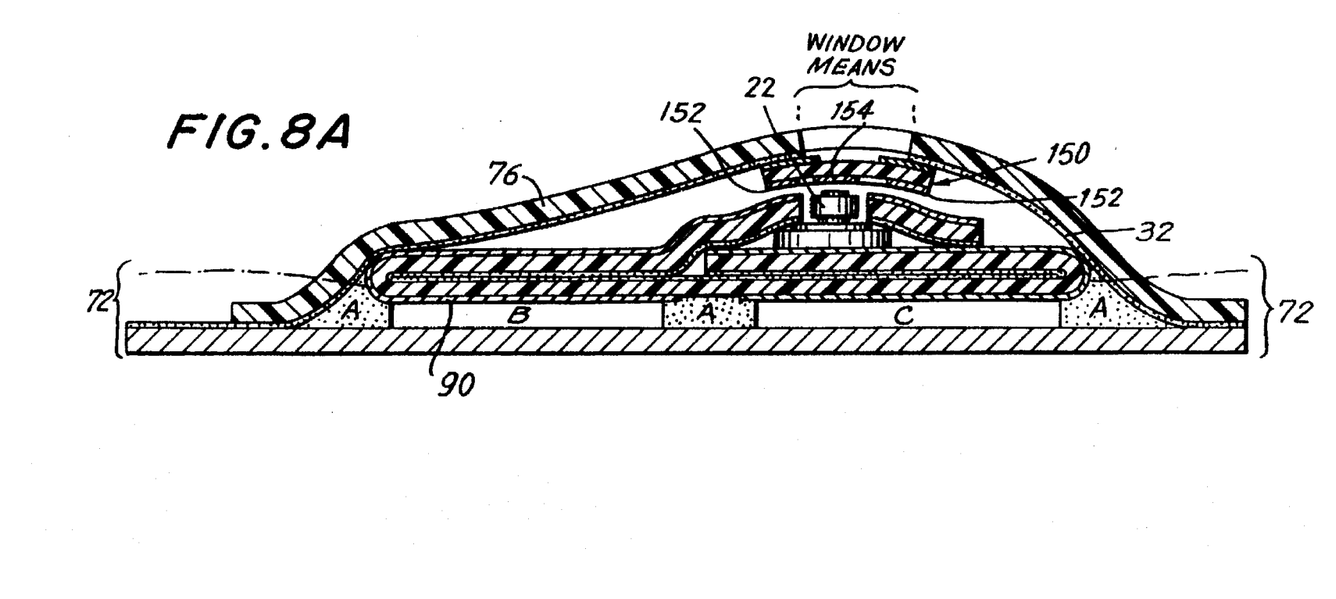
FIG. 8A is a cross-sectional view similar to that shown in FIG. 8, but illustrating an alternate drug applicator construction in which the outer conformal cover has window means through which current induced color changes or other visual feedback information can be viewed for verification of status of the drug delivery system, such as drug delivery taking place or having been terminated.

In FIG. 8A, the cover means 70' is suitably provided with window means, as is shown, which allows the status of the drug applicator to be observed. Such indicator means which is observed through the window means is more particularly described in my earlier filed U.S. patent application, Ser. No. 660,192, filed Oct. 12, 1984. As shown in FIG. 8A, the indicator means 150 is electrically in series with the current conditioning means 22 and conductive surface 90 which powers drug reservoir B. The connections of said indicator means 150 to the current conditioning means 22 and the conductive surface are achieved by means of a suitable flexible conductive adhesive, as is shown at the contact joints 152 and 154.

FIG. 9 represents a like kind of disposable drug applicator 70 having an optionally replaceable drug reservoir sub-assembly 72, as illustrated in FIGS. 8–8A, and a power source or flat layered battery, as as well as electrical or current conditioning means 84 sub-assembly which are secured together by suitable conductive adhesives. In this modification, the battery embodies sheet electrodes such as carbon (+) reference number 86 and zinc (–), reference number 88 and the drug reservoir electrodes 90, 90' are thin and flat. The battery electrodes 86, 88 are adhesively connected to a plastic substrate 30. The webbed material in production is preferably folded along the illustrated longitudinal fold lines, 73, 73', 73", 73'" (and others as may be required depending upon the required number of folds) cut transversely to a predetermined size. One carbon electrode 86 which is connected to the drug reservoir electrode 90 forms a battery with the large zinc electrode 88. The carbon electrode 86 which is connected to electrode 90 could be made as one unitary element. This large zinc electrode 88 is electrically connected to the other carbon electrode 86 by means of the conductive adhesive strip 87 at one end thereof, and thus forms a second battery, in series with the first battery, in conjunction with the small zinc electrode 88 which is likewise electrically connected to conductive surface 134 at 87' or simply with a conductive adhesive strip similar to 87.

It will be apparent to those skilled in the art that most or all of the battery components and connections within the applicator constructions of the invention could be applied by silk screen or rotogravure printing or, printed, die cut and stripped at high speed on standard roll label equipment.

A suitable current or other electronic conditioning means 84 is secured by a conductive adhesive 130 to one of the drug electrode conductive surfaces 90' of flexible plastic substrate 30 and is also electrically connected to one of the battery electrodes, shown at 100 by means of an optional conductive connector 150'. Optionally, a window means, such as a transparent area of the cover 12 or an opening in said cover allows the viewing of an optional indicator 150'. In such case, the indicator 150' replaces the conductive connector. The last battery electrode, shown at 88 is electrically connected to the other drug electrode conductive surface 90 to form a complete electrical circuit between the two drug reservoirs and through the skin. A suitable battery electrode separates element 131 impregnated with a gelled battery electrolyte is inserted between the carbon and zinc electrodes prior to folding, and the peripheries of the battery compartments are suitably sealed at 132 to prevent electrolyte leakage. In this modification, the drug reservoirs are also optionally removable if desired, as was shown in FIGS. 8–8A. It should also be apparent that not only in this modification, some adhesives employed may also be conductive while in other instances it is inherent that the adhesive has no other function than to secure together objects so it need not necessarily be conductive and in some cases it must not be conductive or a short circuit would occur. Also, the voltage of the battery will determine the numbers of carbon and zinc electrodes required, and such voltage can vary depending upon the applications. Although only carbon/zinc batteries are illustrated, other type battery cells could be made in a similar manner.

It will be apparent to those skilled in the art that various combinations of the previously described stages of applicator constructions can be embodied within one drug applicator device. For example, the function of the substrate 48' of FIG. 6 or 7 could be provided by the electrode area 90, 90' of FIG. 10 in which case the addition of the second drug reservoir with its substrate (release liner 48) completes the product. It should also be evident that the construction shown in FIG. 6 or 7 describes the replaceable drug reservoir which is employed by the end user (patient, nurse or doctor) by peeling off the release liner 48, applying the drug reservoir to the area 90, 90' of power supply applicator construction which results in the device shown in FIG. 9 which then could be applied on the human skin after peeling off the release liner 48. In this particular construction, it is envisioned that the battery life will be sufficient for the use of the applicator of FIG. 9 with a predetermined number of "refills" (similar to FIG. 6 or 7) when marketed together in kit form. The same would hold true for all the other alternate constructions and embodiments of the invention. The power supply and the current regulating or electronic conditioning means is designed to perform only for a predetermined number of "refills" so as to guarantee medical supervision for each set of treatments (kit).

A current limiting resistor, in series with the battery can be employed to control the current through the conductive surfaces. Thus, such use would make the device fail safe and could provide current regulation in addition to or instead of solid state conditioning means 22 of FIG. 8. Therefore, if the current conditioning means 22 of FIG. 8 short circuits this resistor will limit the current to a safe value or level.

Although the present invention has been described in some detail by way of illustration and example for purposes of clarity and understanding, it will, of course be understood that various changes and modifications may be made in the form, details, and arrangements of the parts without departing from the scope of the invention as set forth in the following claims.

I claim:

1. A two part transdermal drug applicator for application to the skin of a patient which is electrically powered, comprising: a flexible, non-conductive substrate member having conductive coated areas which together form a single flexible member said flexible member defining first and second surfaces, and said conductive coated areas being on said first surface and forming drug reservoir electrodes, said flexible member being folded in opposite directions at about 180 degrees at each of two opposite ends; and further folded so as to substantially overlie atop itself forming top side and bottom side portions with the conductive coated areas providing electrical conductors between said top side and said bottom side portions, a plurality of separated drug reservoirs forming as a first part a replaceable drug reservoir assembly in electrical contact with said drug reservoir electrodes at said bottom side portions; a reusable/replaceable second part with a power source including at least one battery having positive and negative terminals in an electrical circuit, connected to said electrical conductors at said top side portions with said power source connected to said top side portions via passage means in said flexible member for enabling electrical connections to the top side portions of both oppositely folded ends for providing current to said plurality of separated drug reservoirs via said conductors and said drug reservoir electrodes, electrical current conditioning means in said circuit with said power source and drug reservoir electrodes, and a covering for said drug applicator enveloping and enclosing said flexible member, said power source and said current conditioning means, and said plurality of drug reservoirs leaving a side of said drug reservoirs free for application; whereby both said first and second parts are replaceable when exhausted in use.

2. The transdermal drug applicator according to claim 1, further including a programmable control means connected to said power source for programming control of said power source for said drug applicator.

3. The transdermal drug applicator according to claim 1, wherein said drug reservoirs include gels.

4. The transdermal drug applicator according to claim 3, wherein said gels are reinforced by scrims.

5. The transdermal drug applicator according to claim 3, wherein said drug reservoirs include open cell foam material impregnated with said gels.

6. The transdermal drug applicator according to claim 5, further including a semi-permeable membrane in juxtaposition to said drug reservoirs, said semipermeable membrane having seals so as to define particular drug zones.

7. The transdermal drug applicator according to claim 6, wherein said drug zones contain drugs of different compositions from each other.

8. The transdermal drug applicator according to claim 6, wherein said drug zones contain drugs of different concentrations from each other.

9. The transdermal drug applicator according to claim 1, further including another substrate containing thereon a coated release agent, and said plurality of drug reservoirs being positioned with their free sides in juxtaposition with said release agent of said another substrate.

10. A transdermal drug applicator according to claim 9, wherein said topside portions of said coated areas are joined to said positive and negative terminals of said power source so as to create an electrical circuit when said applicator is applied to the skin.

11. A transdermal drug applicator according to claim 1, wherein some of the conductors are of a predetermined resistance so as to perform the function of a current limiting resistor.

12. The transdermal drug applicator according to claim 1, further including an adhesive layer on the other side of said non-conductive substrate for firmly securing said folded opposite ends of said non-conductive substrate to itself.

13. The transdermal drug applicator according to claim 1, further including a conductive adhesive at opposite end portions of said conductive coated areas for removably securing said plurality of drug reservoirs to said conductive coated areas.

14. The transdermal drug applicator according claim 1, wherein said electrical circuit includes indicator means in said electrical circuit for indicating the operational status of said drug applicator.

15. The transdermal drug applicator according to claim 14, wherein said indicator means is visible through aperture means provided in said covering.

16. The transdermal drug applicator according to claim 15, wherein said indicator means is electrically in series with said current conditioning means and said top side electrical conductor.

17. The transdermal drug applicator according to claim 16, wherein said indicator means is connected to said current conditioning means and said top side electrical conductor by means of conductive adhesive at joint contact points.

* * * * *